United States Patent [19]

Greenberg

[11] Patent Number: 4,991,234
[45] Date of Patent: Feb. 12, 1991

[54] BODY SUPPORT BAND

[76] Inventor: Bert Greenberg, 2030 S. Ocean Dr., Hallandale, Fla. 33009

[21] Appl. No.: 418,845

[22] Filed: Oct. 10, 1989

[51] Int. Cl.$^5$ .......................................... A41D 00/00
[52] U.S. Cl. ............................................ 2/170; 2/16; 2/311; 128/157
[58] Field of Search ............ 2/16, 44, 92, 170, 161 A, 2/312, 338; 128/157, 889; 450/82, 83, 84, 85

[56] References Cited

U.S. PATENT DOCUMENTS

| | | | |
|---|---|---|---|
| 1,753,739 | 4/1930 | Burns | 2/312 |
| 3,086,529 | 4/1963 | Munz et al. | 2/311 X |
| 3,256,882 | 6/1966 | Huber | 2/16 |
| 3,298,366 | 1/1967 | Moore et al. | 128/157 |
| 3,417,749 | 12/1968 | Bailey | 128/157 |
| 3,442,270 | 5/1969 | Steinman | 128/157 |
| 3,480,012 | 11/1969 | Smithers et al. | 128/157 |
| 3,509,875 | 5/1970 | Richter | 2/311 X |
| 3,512,776 | 1/1968 | Thomas, Sr. | 2/161 A |
| 3,554,190 | 1/1971 | Kaplan | 2/44 X |
| 3,561,436 | 2/1971 | Gaylord, Jr. | 128/157 |
| 3,561,442 | 2/1971 | Goswitz | 128/157 |
| 3,603,316 | 9/1971 | Lehman | 2/338 |
| 4,273,130 | 6/1981 | Simpson | 2/338 X |
| 4,384,583 | 5/1983 | Speelman et al. | 2/338 X |
| 4,400,831 | 8/1983 | Rietz | 2/161 A |
| 4,408,358 | 10/1983 | Swan | 2/161 A |
| 4,525,877 | 7/1985 | Chong | 2/161 A |
| 4,608,720 | 9/1986 | Purin | 2/161 A |
| 4,627,109 | 12/1986 | Carabelli et al. | 2/44 |
| 4,632,105 | 12/1986 | Barton | 128/157 R |
| 4,782,535 | 11/1988 | Yewer, Jr. et al. | 2/321 |
| 4,787,381 | 11/1988 | Hubbard et al. | 128/157 |
| 4,829,604 | 5/1989 | Allen et al. | 2/170 |
| 4,836,194 | 6/1989 | Sebastian et al. | 2/338 X |
| 4,843,651 | 7/1989 | Gramza et al. | 2/161 A |

*Primary Examiner*—Werner H. Schroeder
*Assistant Examiner*—Jeanette E. Chapman
*Attorney, Agent, or Firm*—McAulay Fisher Nissen & Goldberg

[57] ABSTRACT

A support band is disclosed having elastic portions and hook and loop fastener portions for encircling a portion of a wearer's body. One hook segment is positioned adjacent to the terminating end of the band and another hook segment is positioned intermediate between the starting and terminating ends of the band. One portion of the loops is positioned adjacent the starting end of the band and another portion of the loops is positioned intermediate between the starting and terminating ends of the band. The band forms a tubular support device encircling the body portion wherein the intermediate hook segment engages the starting end portion of the loops after the initial wrap of the band to form an anchor point, and the terminating end hook segment engages an intermediate portion of the loops upon final wrapping of the band, said wrappings being made with the band under tension.

9 Claims, 5 Drawing Sheets

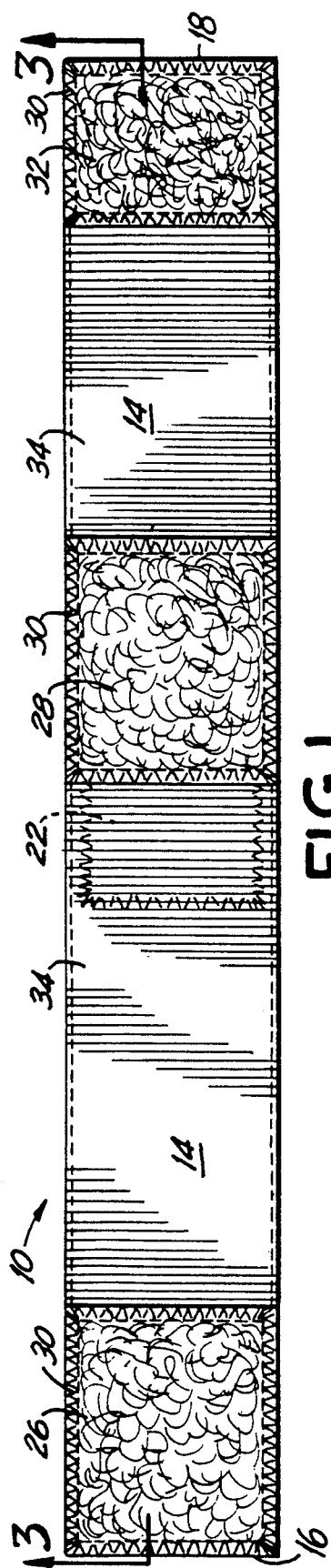
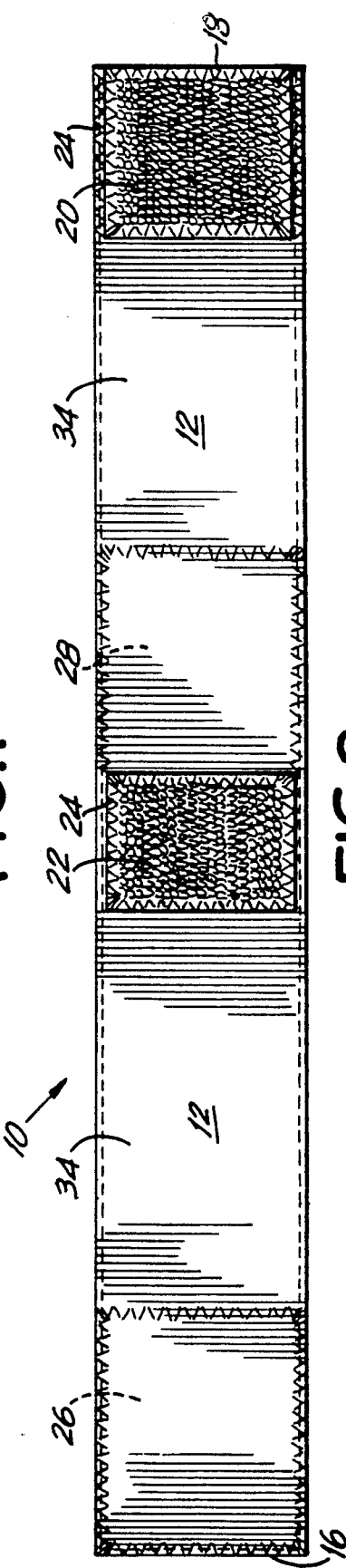
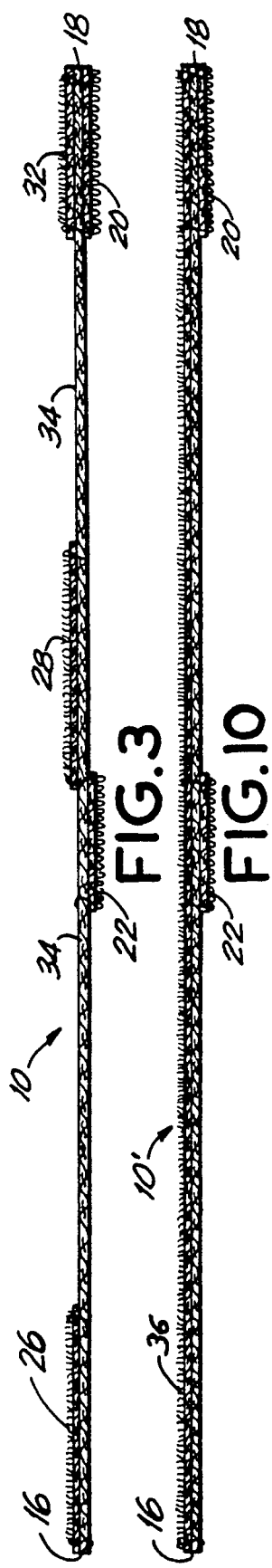
FIG.1
FIG.2
FIG.3
FIG.10

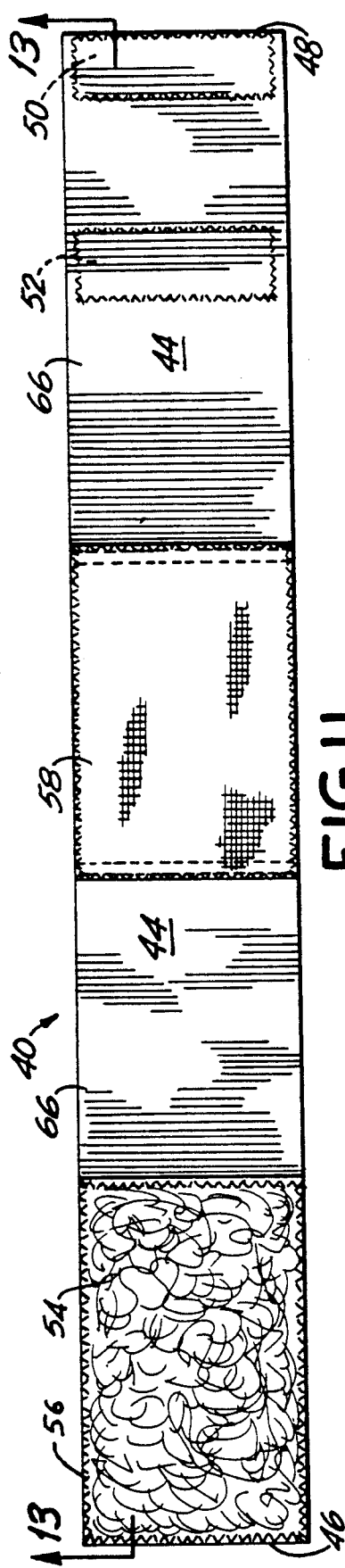
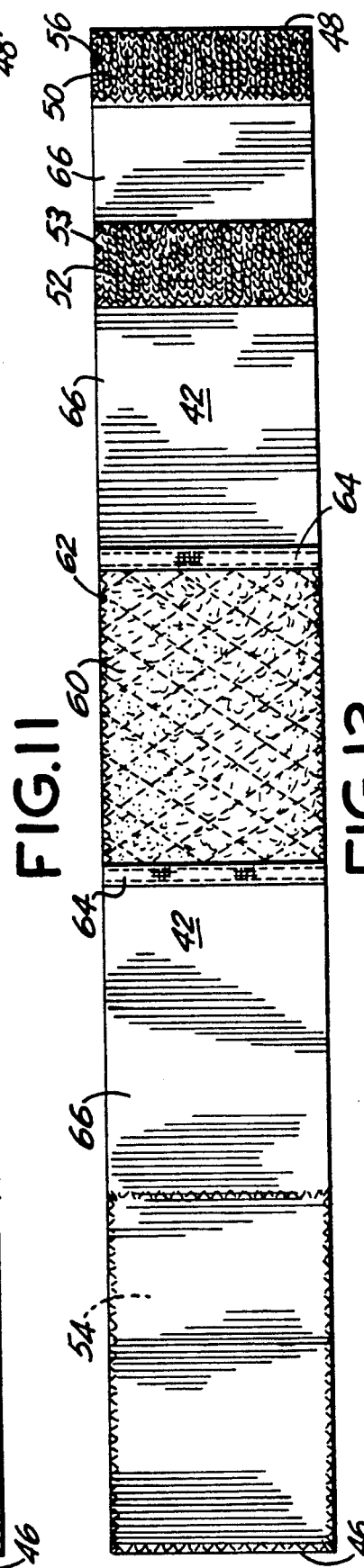
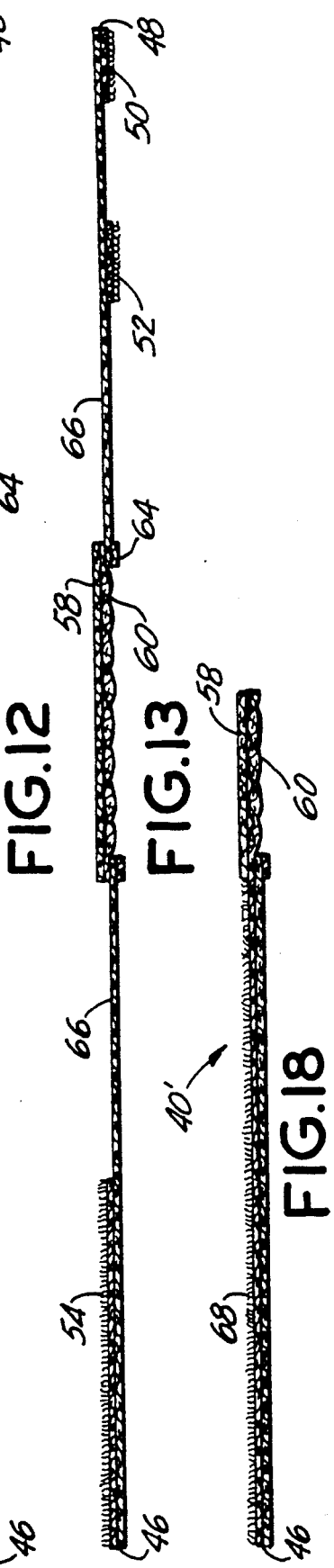
FIG.11  FIG.12  FIG.13  FIG.18

BODY SUPPORT BAND

BACKGROUND OF THE INVENTION

I. Field of the Invention

This invention relates generally to a support band and, more particularly, to a support band having elastic portions and hook and loop fastener portions for encircling a portion of a wearer's body.

II. Description of the Prior Art

It is known to provide elastic bandages which function as a support band for encircling a portion of a wearer's body; such as, the wrist or ankle. The band may be retained in its convoluted or wrapped position on the wearer's body by retaining clips. Alternatively, the band may be provided with hook and loop fastener portions which interengage for keeping the band in place when in use.

Support bands of the known type typically are used when the body portion, such as the wrist, is injured or sprained. Wrapping the band around the wrist restricts movement of the ligaments and tendons to reduce pain. The wrapped band also affords cushioning to the injured area. In some instances, tightening of the body area by means of a wrapped band permits greater strength or force exerted by the muscles due to restricted motion of the ligaments and tendons.

While the known elastic bandages provide some relief to an injured or weak wrist, they are not entirely satisfactory. It has been found that the continuous wrapping of an elastic band is not truly effective in strengthening the wrist. Rather, it has been found that increased muscle strength is achieved if the band is first anchored after the initial wrap from which anchor the band may then be finally fastened under tension.

In some known elastic bandages, a tubular cuff is first fitted around the body portion and the starting end of the band is anchored to the cuff prior to wrapping of the band. However, here again, the wrapping proceeds continuously without further anchoring of the band until it is fully or finally wrapped.

The present invention improves on these known devices and enables the wearer to exert increased muscle strength by providing a support band which is anchored after the initial wrap and prior to final wrapping under tension in the manner hereinafter described.

SUMMARY OF THE INVENTION

The support band of the present invention includes a band having elastic portions and hook and loop fastener portions. A plurality of separate hook segments of said hook and loop fasteners are provided on a first surface of the band. One of said hook segments is positioned adjacent to the terminating end of the band and another one of said hook segments is positioned intermediate between the starting and terminating ends of the band. The starting end of the band is free of any hook segments.

A plurality of loops of said hook and loop fasteners are provided on a second surface of the band opposite to said first surface. One portion of said loops is positioned adjacent to the starting end of the band and another portion of said loops is positioned intermediate between the starting and terminating ends of the band.

The band forms a tubular support device encircling a body portion of the wearer wherein the intermediate hook segment engages the starting end portion of the loops after the initial wrap of the band to form an anchor point, and the terminating end hook segment engages the intermediate portion of the loops upon final wrapping of the band, said wrappings being made with the band under tension.

The loop portions of the hook and loop fasteners may form one continuous loop segment or a plurality of separate loop segments. Also, a heat insulating panel may be positioned intermediate between the starting end of the band and the intermediate hook segment for added comfort and support, such as when the band is worn encircling the wearer's waist with the insulating panel positioned against the wearer's lower back.

Additional features and advantages of the present invention will become apparent from a consideration of the following detailed description when taken in conjunction with the accompanying drawings.

BRIEF DESCRIPTION OF THE DRAWINGS

FIG. 1 is a top plan view of the support band constructed in accordance with the present invention;

FIG. 2 is a bottom plan view of the support band of FIG. 1;

FIG. 3 is a sectional view taken along line 3—3 of FIG. 1;

FIG. 10 is a view similar to FIG. 3 showing another embodiment of the support band;

FIG. 11 is a top plan view of another support band representing yet another embodiment of the invention;

FIG. 12 is a bottom plan view of the support band of FIG. 11;

FIG. 13 is a sectional view taken along line 13—13 of FIG. 11;

FIG. 18 is a partial view similar to FIG. 13 showing another embodiment of the support band.

DESCRIPTION OF THE PREFERRED EMBODIMENT

Figure 4:
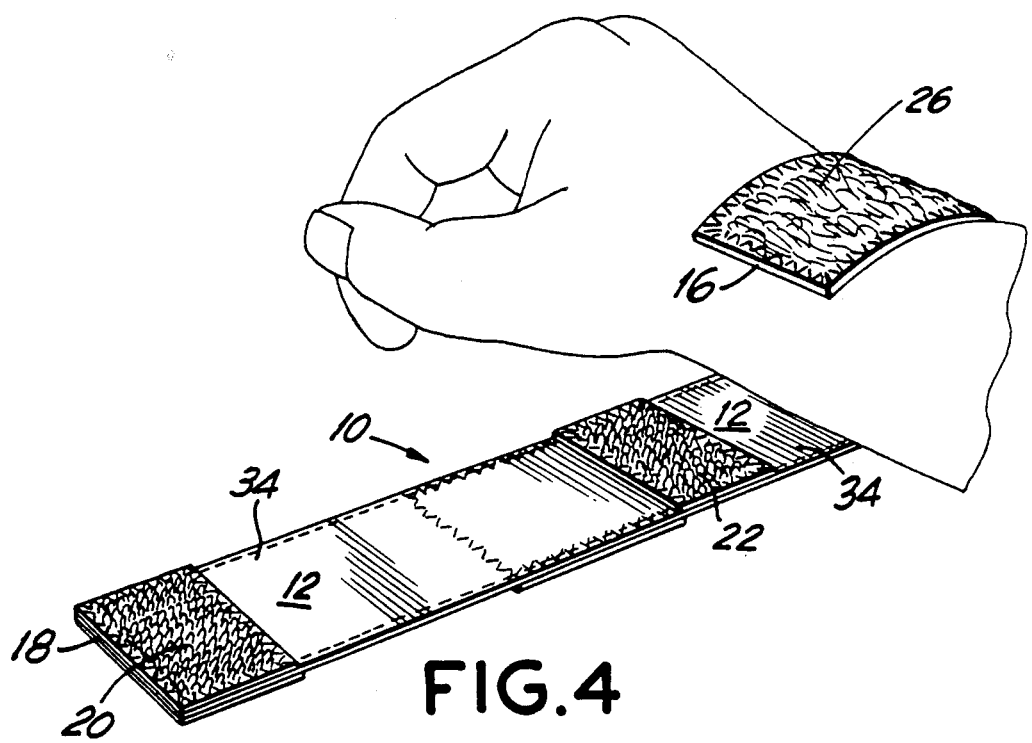
FIG. 4 is a perspective view of the band of FIG. 1 positioned on the wearer's wrist prior to wrapping.
Figure 5:
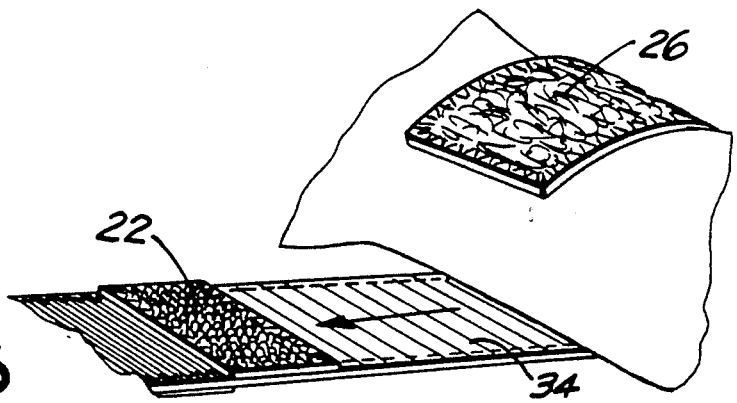
FIG. 5 is a partial view similar to FIG. 4 showing the band under tension during the initial wrap.

Referring to the drawings, numeral 10 represents a support band constructed in accordance with the present invention. Band 10 is flexible and is made of woven or knitted fabric, such as nylon or other synthetic yarn, also having elastic yarn. For the embodiment of FIGS. 1-10, the band preferably is 2 to 3 inches (5.08 to 7.63 cm) in width and has a length sufficient to wrap twice around a wearer's wrist. Since the size of a wearer's wrist varies from person to person, it is envisioned that the band may be constructed of various lengths to accommodate small, medium and large size wrists. Thus, for example, a band to accommodate a small size wrist would be approximately 17 inches (43.18 cm) in length. These dimensions are purely illustrative and are not to be deemed limitations on the invention.

Band 10 may be regarded as being formed having a first surface 12, a second surface 14, a starting end 16 and a terminating end 18. A plurality of separate hook segments 20 and 22 are affixed or secured to band surface 12 by stitching 24 or the like. As shown in FIGS. 2, 3, 4 and 6, hook segment 20 is positioned adjacent to the terminating end 18 of band 10 and hook segment 22 is positioned intermediate between the staring end 16 and the terminating end 18 of the band. The starting end 16 of band 10 is free of such hook segments for reasons that will hereinafter become apparent.

A plurality of separate loop segments 26 and 28 are affixed or secured to band surface 14 by stitching 30 or the like. As shown in FIGS. 1, 3, 4 and 6, loop segment 26 is positioned adjacent to the starting end 16 of band 10 and loop segment 28 is positioned intermediate between the staring end 16 and the terminating end 18 of the band. The portions of band 10 disposed between the hook and loop segments are represented by numeral 34 and are elastic. Hook and loop segments 22 and 26 and hook and loop segments 20 and 28 represent, respectively, interengaging hook and loop fasteners for anchoring and then wrapping band 10 in place on a portion of the wearer's body under tension as hereinafter described.

Figure 8:
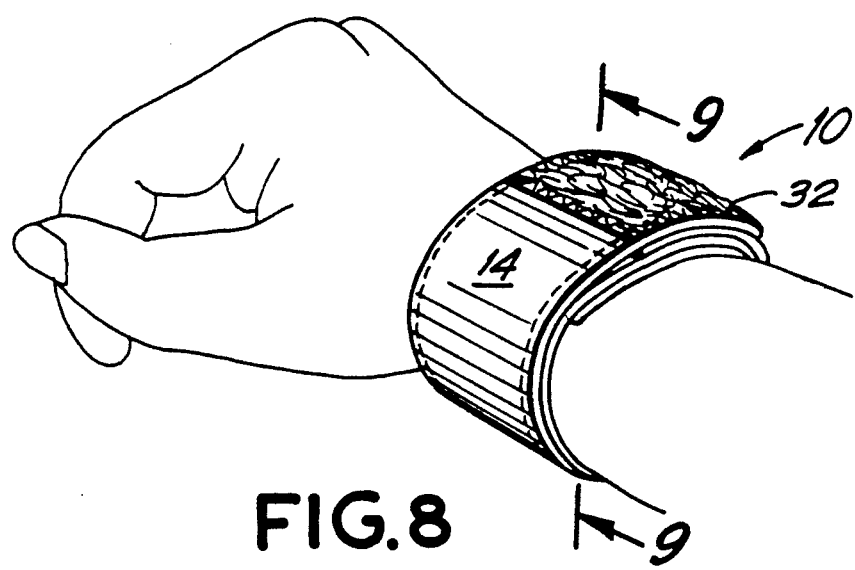
FIG. 8 is a view similar to FIG. 7 showing the band finally wrapped and fastened.
Figure 9:
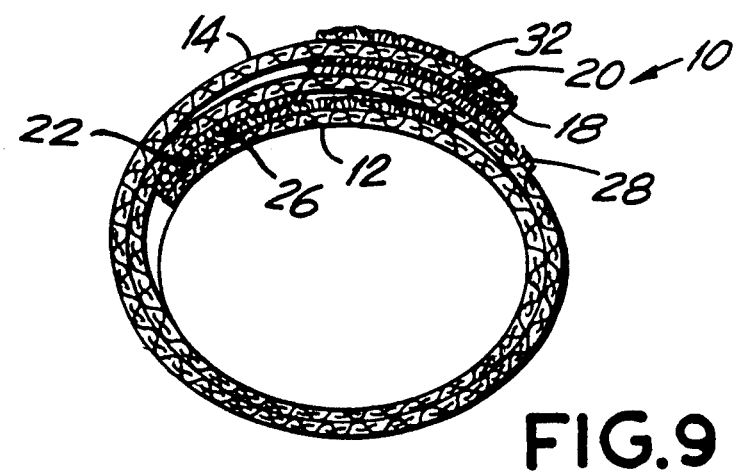
FIG. 9 is a sectional view taken along line 9—9 of FIG. 8 showing the wrapped band as a convolute tubular support device with the body portion removed for purposes of clarity.

If desired, a third loop segment 32 may be positioned adjacent to the terminating end 18 of band 10 and secured to band surface 14 by stitching 30. However loop segment 32 is not for engagement with any of the hook segments and is merely to provide additional cushioning, if desired, as shown in FIGS. 8 and 9.

The manner of wrapping band 10 on the wearer's wrist is shown in FIGS. 4-8. Starting end 16 is placed on the wrist with the first surface 12 facing and in contact with the skin. As such, it will now become apparent that since staring end 16 is not intended to connect with or become anchored to any other member, the placement of hook segments at said starting end 16 is unnecessary and, indeed, would present discomfort to the wearer if they were present.

Figure 6:
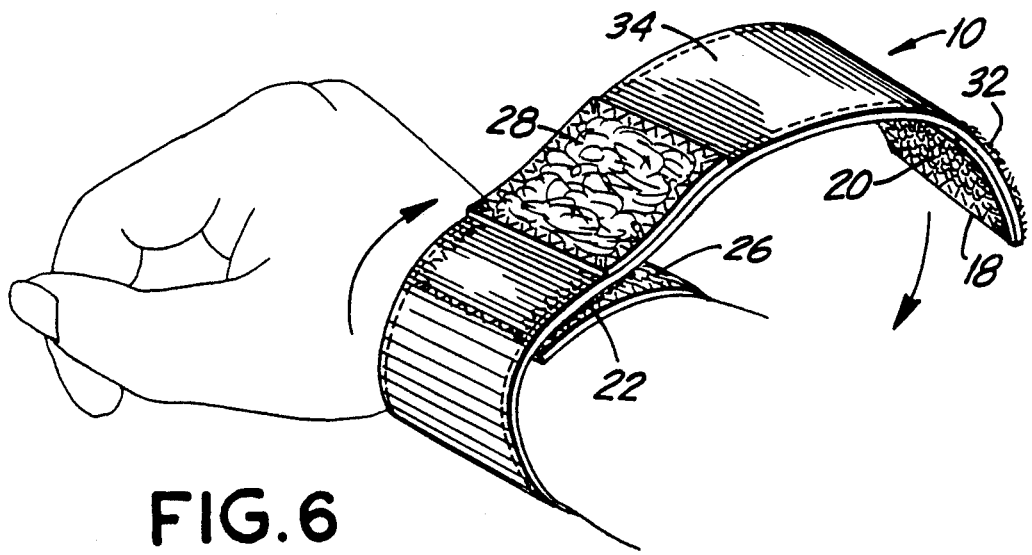
FIG. 6 is a view similar to FIG. 4 with the band anchored by interengaging hook and loop fasteners after the initial wrap.
Figure 7:
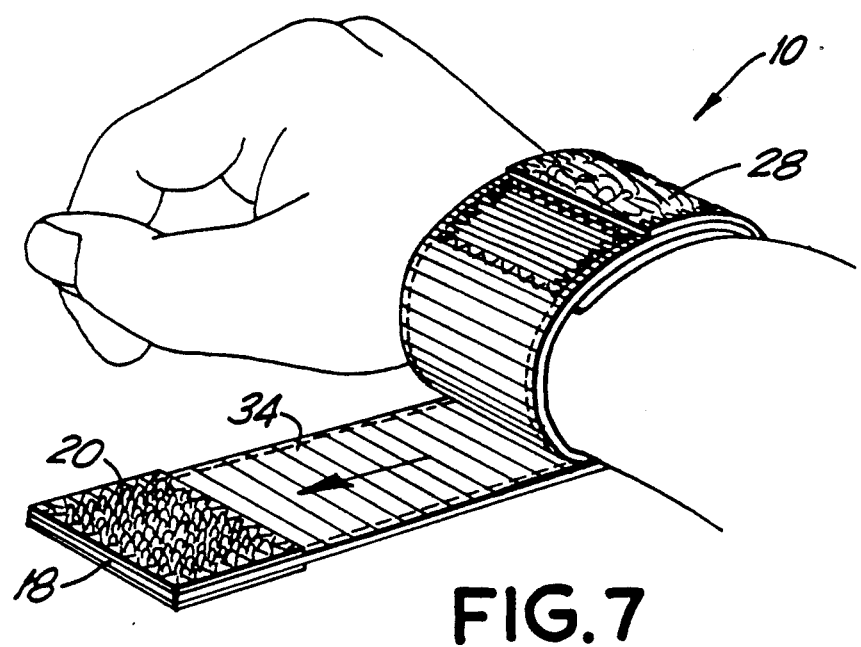
FIG. 7 is a view similar to FIG. 6 showing the band under tension after the initial wrap.

With staring end 16 held in place, either by the wearer's fingers or by another party assisting in the wrapping (not shown), band 10 is tensioned and wrapped to cause the intermediate hook segment 22 to engage the starting end loop segment 26. This constitutes the first engagement of the hook and loop fastener portions, as shown in FIG. 6, and provides the anchor for further wrapping of band 10 under increased tension.

Band 10 is now further wrapped to cause the terminating end hook segment 20 to engage the intermediate loop segment 28. This constitutes the second engagement of the hook and loop fasteners as shown in FIG. 8. The arrangement is such that band 10 forms a convolute tubular support member, as shown in FIG. 9, with band surface 12 constituting at the starting end 16 the inner and inward facing end of the support member, and band surface 14 constituting at the terminating end 18 the outer and outward facing end of said member. It is contemplated that in wrapping band 10, the tension in the band should be made greater when the second hook and loop fastener engagement is made then when the first hook and loop fastener engagement is made. This increased tightening of band 10, which is made possible because of the anchoring effect of the first engagement of the hook and loop fasteners 22 and 26, permits greater strength or force exerted by the wearer's muscles due to the restricted motion of the ligaments and tendons. Such increased strength is particularly desirable for persons engaged in sporting events, such as tennis, baseball and golf, as well as persons having weak or injured wrists. The tension imparted to band 10 during wrapping should not be so great as to restrict movement of the wrist. That is, the final wrapping should still permit the band to be further tensioned by motion of the wrist, such as when swinging a baseball bat, and then return to a less tensioned state when the wrist is at rest.

As is further apparent from the drawings, particularly FIG. 9, the intermediate hook segment 22 and the intermediate loop segment 28 are positioned at least 360° from the starting end 16 of band 10, and the terminating end hook segment 20 is positioned at least 720° from the starting end of said band.

FIG. 10 shown an alternative embodiment of the band designed by number 10' wherein in place of separate loop segments 26, 28 and 32, there is provided on band surface 14 a plurality of loops 36 extending for the entire length of the band. As such, the various loop segments of FIGS. 1-9 would now be regarded merely as portions of loops 36. Also, the portions of band 10' between the starting end 16 and hook segment 22, and between hook segments 20 and 22 are elastic. In all other aspects, band 10' of FIG. 10 is constructed the same as band 10. Alternatively, band 10' may be constructed of an elastic fabric material having the loops 36 as part of the material.

FIGS. 11-18 show another embodiment of the band designated by numeral 40 adapted for use in association with the wearer's waist. Band 40 is constructed of the same material as band 10 but is preferably made having a width of approximately 6 inches (15.24 cm). The length of band 40 will vary and will come in various lengths to accommodate small, medium and large size waists.

Band 40, similar to band 10, has a first surface 42, a second surface 44, a starting end 46 and a terminating end 48. A plurality of hook segments 50 and 52 are affixed to band surface 42 by stitching 53. Hook segment 50 is positioned adjacent to the terminating end 48 of band 40 and hook segment 52 is positioned intermediate between the starting end 46 and the terminating end 48 of the band. As was the case with band 10, the starting end 46 of band 40 is free of such hook segments.

Figure 17:
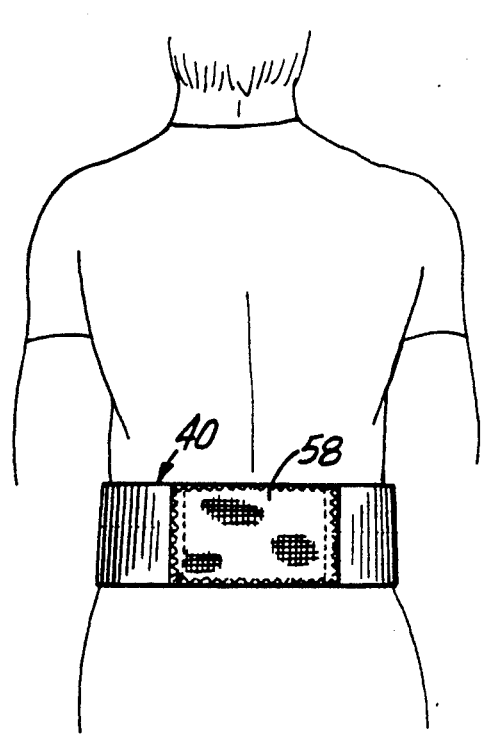
FIG. 17 is a view similar to FIG. 16 looking at the back of the wearer.

A plurality of loops 54 are affixed to band surface 44 by stitching 56 adjacent to the starting end 46. Disposed intermediate between starting end 46 and hook segment 52, on band surface 44, is a heat insulating panel 58 made of nonelastic material and having insulating material 60. Panel 58 is sewn in place by stitching 62 and vertically stitched webbing 64. When band 40 is wrapped in place, panel insulating material 60 is positioned such that is constitutes the inner face of the convolute tubular support device and comes in contact with the lower region of the wearer's back, as shown in FIG. 17. Panel 58 not only provides added support for the lower back but also prevents the loss of significant body heat from the region where the panel contacts the body. The portions of band 40 to either side of panel 58, and between the hook segments 50 and 52, represented by numeral 66, are elastic.

Figure 14:
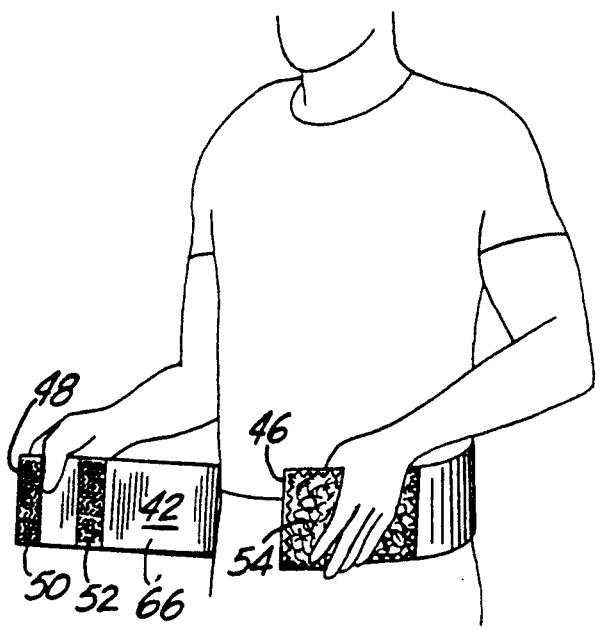
FIG. 14 is a perspective view of the band of FIG. 11 positioned on the wearer's waist prior to wrapping.
Figure 15:
FIG. 15 is a view similar to FIG. 14 showing the band anchored by interengaging hook and loop fasteners after the initial wrap.
Figure 16:
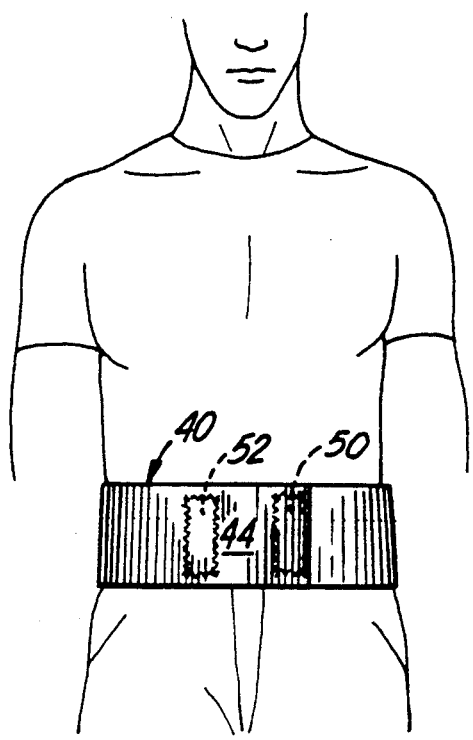
FIG. 16 is a view showing the band finally wrapped and fastened looking at the front of the wearer.

The manner of wrapping band 40 around the wearer's waist is shown in FIGS. 14–16. Starting end 46 is placed on the abdomen with the band surface 42 facing and in contact with the body. Band 40 is then tensioned and wrapped to cause intermediate hook segment 52 to engage a portion of loops 54. This constitutes the first engagement of the hook and loop fasteners, as shown in FIG. 15, and provides the anchor for further wrapping of band 40 under increased tension.

Band 40 is now further tensioned to cause the terminating end hook segment 50 to engage another portion of loops 54. This constitutes the second engagement of the hook and loop fasteners as shown in FIG. 16. As was the case with band 10, the intermediate hook segment 52 is positioned at least 360° from the starting end 46 of the band.

It will be appreciated that panel 58 may be constructed without heat insulating qualities, but which nonetheless would be nonelastic to provide added support.

FIG. 18 shows an alternative embodiment of the band of FIG. 11, designated by numeral 40', wherein the loops 68 extend from the staring end 46 to the intermediate panel 58. The portion of band 40' associated with loops 68 may also be made elastic similar to elastic portion 66. In all other aspects, band 40' of FIG. 18 is constructed the same as band 40.

While preferred embodiments of the invention have been shown and described in detail, it will be readily understood and appreciated that numerous omissions, changes, and additions may be made without departing from the spirit and scope of the invention.

I claim:

1. A flexible support band for encircling a portion of a wearer's body, said band comprising:
   a single band having elastic portions and hook and loop fastener portions, said band having solely two end defining a starting end and a terminating end, and said band having a first surface and a second surface opposite to said first surface;
   said first surface of said band having a plurality of one of said hook and loop fastener portions extending to said terminating end of said band and another one of said same fastener portions being intermediate between said starting and terminating ends of said band;
   said second surface of said band having a plurality of the other one of said hook and loop fastener portions extending to said starting end of said band and another one of said same other fastener portions being intermediate between said starting and terminating ends of said band;
   said band forming a convolute tubular support device encircling a body portion of the wearer, said first surface of said band constituting at said starting end an inner and inward facing end of said convolute tubular support device and said second surface of said band constituting at said terminating end an outer and outward facing end of said convolute tubular support device;
   the intermediate band portion containing said one of said hook and loop fastener portions engaging the starting end portion of said band containing said other one of said hook and loop fastener portions, and said terminating end portion of said band containing said one of said hook and loop fastener portions engaging the intermediate band portion containing said other one of said hook and loop fastener portions;
   whereby the engagement of said intermediate band portion with said starting end portion of said band constitutes a first engagement of said hook and loop fastener portions and the engagement of said terminating end portion of said band with said intermediate band portion constitutes a second engagement of said hook and loop fastener portions, said band being under tension when the second engagement of said hook and loop fastener portions is made.

2. The support band of claim 1, wherein said band also is under tension when the first engagement of said hook and loop fastener portions is made, the tension in said band being greater when the second engagement of said hook and loop fastener portions is made than when the first engagement of said hook and loop fastener portions is made.

3. The support band of claim 1, wherein the intermediate band portions containing said hook and loop fastener portions are positioned at least 360° from the starting end of said band and said terminating end band portion is positioned at least 720° from the starting end of said band when said band is worn on the wearer's body.

4. A flexible wrist support band comprising;
   a single band having elastic portions and hook and loop fastener portions, said band having solely two ends defining a starting end and a terminating end, and said band having a first surface and a second surface opposite to said first surface;
   said first surface of said band having a plurality of separate hook portions of said hook and loop fastener portions, one of said hook portions extending to said terminating end of said band and another one of said hook portions being intermediate between said starting and terminating ends of said band;
   said second surface of said band having a plurality of loop portions of said hook and loop fastener portions, one of said loop portions extending to said starting end of said band and another one of said loop portions being intermediate between said starting and terminating ends of said band;
   said band forming a convolute tubular support device encircling a wearer's wrist, said first surface of said band constituting at said starting end an inner and inward facing end of said convolute tubular support device and said second surface of said band constituting at said terminating end an outer and outward facing end of said convolute tubular support device;
   said intermediate hook portion engaging said starting end loop portion and said terminating end hook portion engaging said intermediate loop portion;
   said intermediate hook portion and said intermediate loop portion being positioned at least 360° from the starting end of said band when said band is worn on a wearer's wrist;
   whereby the engagement of said intermediate hook portion with said starting end loop portion constitutes a first engagement of said hook and loop fastener portions and the engagement of said terminating end hook portion with said intermediate loop portion constitutes a second engagement of said hook and loop fastener portions, said band being under tension when the second engagement of said hook and loop fastener portions is made.

5. The wrist support band of claim 4, wherein said second surface of said band has another one of said loop fastener portions adjacent to said terminating end of said band.

6. The wrist support band of claim 4, wherein said plurality of loop portions comprises separate loop portions.

7. The wrist support band of claim 4, wherein said terminating end hook portion is positioned at least 720° from the starting end of said band when said band is worn on the wearer's wrist.

8. The wrist support band of claim 4, wherein said band also is under tension when the first engagement of said hook and loop fastener portions is made, the tension in said band being greater when the second engagement of said hook and loop fastener portions is made than when the first engagement of said hook and loop fastener portions is made.

9. The wrist support band of claim 8, wherein said starting end of said band is free of said hook portions.

* * * * *